US 8,090,544 B2

(12) United States Patent
Nagai et al.

(10) Patent No.: US 8,090,544 B2
(45) Date of Patent: Jan. 3, 2012

(54) METHOD FOR DETERMINING CONCENTRATION OF IMPURITY ELEMENT

(75) Inventors: Kiyoshi Nagai, Kanagawa (JP); Tetsuo Ishida, Kanagawa (JP)

(73) Assignee: Komatsu Electronic Metals Co., Ltd., Kanagawa (JP)

( * ) Notice: Subject to any disclaimer, the term of this patent is extended or adjusted under 35 U.S.C. 154(b) by 904 days.

(21) Appl. No.: 11/569,827

(22) PCT Filed: Jun. 2, 2005

(86) PCT No.: PCT/JP2005/010146
§ 371 (c)(1),
(2), (4) Date: Nov. 30, 2006

(87) PCT Pub. No.: WO2005/119229
PCT Pub. Date: Dec. 15, 2005

(65) Prior Publication Data
US 2009/0198452 A1    Aug. 6, 2009

(30) Foreign Application Priority Data
Jun. 3, 2004  (JP) .................. 2004-166145

(51) Int. Cl.
*G01N 31/00* (2006.01)
(52) U.S. Cl. ........................................................ 702/23
(58) Field of Classification Search .................. 702/23, 702/28, 30, 31, 134, 182, 183, 193; 438/149, 438/287, 386, 480; 257/410; 436/72; 250/282
See application file for complete search history.

(56) References Cited

U.S. PATENT DOCUMENTS

| | | | |
|---|---|---|---|
| 4,733,073 A * | 3/1988 | Becker et al. | 250/288 |
| 5,350,919 A * | 9/1994 | Hirano et al. | 250/282 |
| 6,035,246 A | 3/2000 | Wagner | 700/266 |
| 2003/0008404 A1* | 1/2003 | Tomita et al. | 436/72 |

FOREIGN PATENT DOCUMENTS

| | | |
|---|---|---|
| EP | 0 878 827 | 11/1998 |
| EP | 1 154 256 | 11/2001 |
| JP | 09-021768 | 1/1997 |
| JP | 2001-021460 | 1/2001 |

OTHER PUBLICATIONS

Toray Research Center, "Microanalysis of Atmospheric Component Element in Semiconductor Material", [online], [retrieved on Jun. 3, 2004], Internet<URL: http://www.toray-research.co.jp/sims/pdf/taikiseibun.pdf>.

International Search Report, PCT/JP2005/010146, Aug. 2005.

* cited by examiner

*Primary Examiner* — Mohamed Charioui
(74) *Attorney, Agent, or Firm* — Occhiuti Rohlicek & Tsao LLP

(57) ABSTRACT

A method for shortening a waiting time from the setting of a sample in a chamber to the stabilisation of the intensity for a secondary ion for SIMS analysis (mass analysis of the secondary ion) using a raster variation method is provided. By approximating so that the difference between time-lapse variations in intensities of the secondary ions sequentially measured for irradiation densities of two different primary ions becomes constant, a method capable of carrying out an accurate measurement of the concentration of an impurity in consideration of background noise despite time-lapse variations in the intensities of the secondary ions is provided.

12 Claims, 14 Drawing Sheets

Wide Raster

Narrow Raster

FIG. 5

A Region

| Report | Left step | Right step |
|---|---|---|
| [C] (a/cm3) | 9.38E+14 | 9.38E+14 |
| [C]BG | 3.01E+15 | 2.88E+15 |
| Time(sec) | 1858.168 | 2475.687 |

FIG. 7

B Region

| Report | Left step | Right step |
|---|---|---|
| [C] (a/cm3) | 9.62E+14 | 9.62E+14 |
| [C]BG | 2.36E+15 | 2.35E+15 |
| Time(sec) | 14472.382 | 15089.900 |

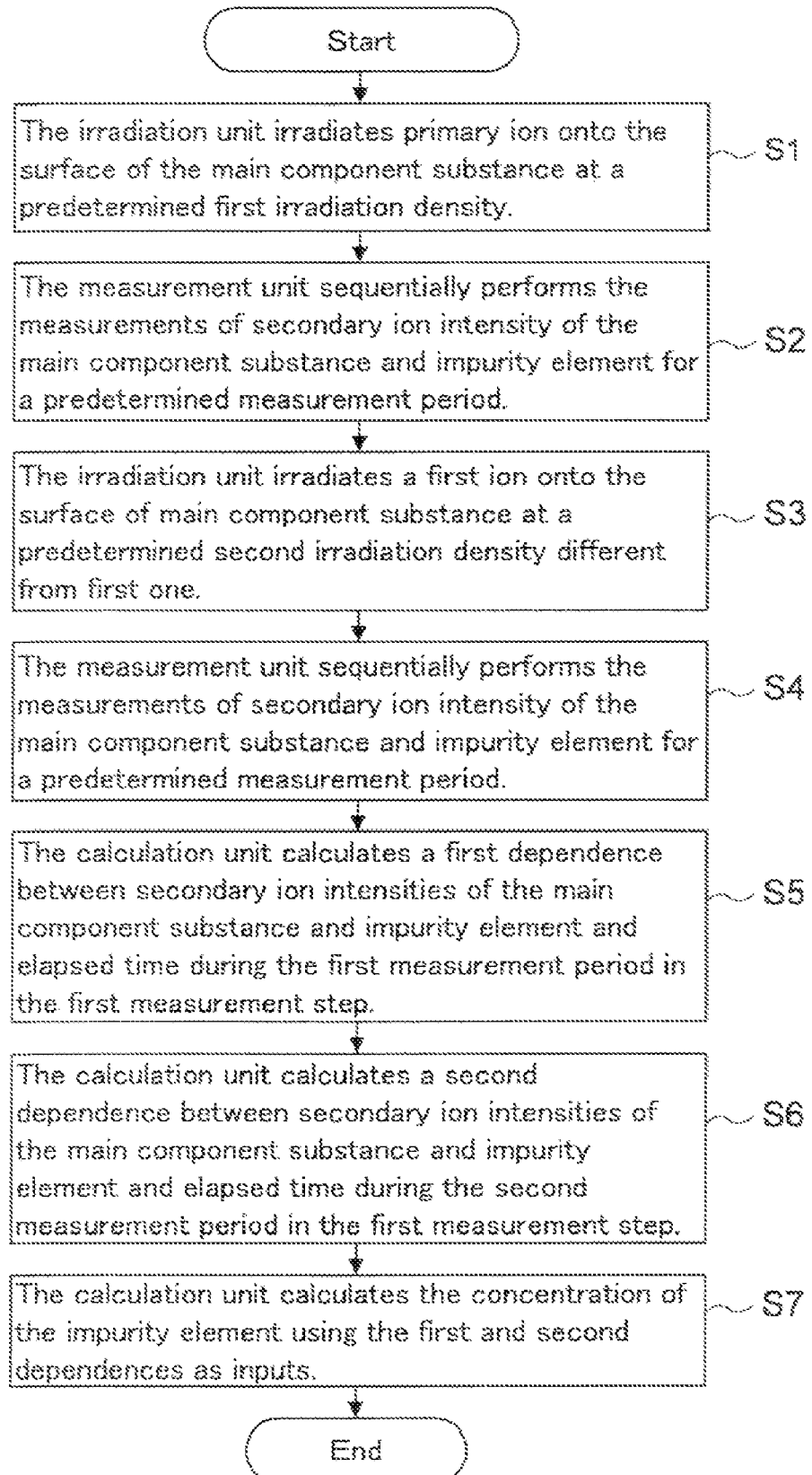

FIG. 12

| Element | Measured Sample | Error of only Narrow Region | 99% Confident Limit* of Narrow and Wide Region |
|---|---|---|---|
| Carbon | 46 | 1.2E+16 a/cc | 2.8E+14 a/cc |
| Copper | 2 | 6.7E+14 a/cc | 1.4E+14 a/cc |
| Nitrogen | 6 | 5.2E+14 a/cc | 1.3E+14 a/cc |

* Results obtained by calculation with 1% risk rate.

METHOD FOR DETERMINING CONCENTRATION OF IMPURITY ELEMENT

CROSS-REFERENCE TO RELATED APPLICATIONS

This application is the National Stage of International Application No. PCT/JP2005/010146, filed on Jun. 2, 2005, which claims the benefit of Japan Application Serial No. 2004-166145, filed on Jun. 3, 2004.

TECHNICAL FIELD

The present invention relates to a method for determining the concentration of an impurity substance included in a primary component substance.

BACKGROUND ART

SIMS (Secondary Ion Mass Spectrometry) has been used as means capable of quickly analyzing the concentrations of impurities at high sensitivities for evaluating many electronic materials including send conductor materials. As shown in FIG. 1, in SIMS, a primary ion is irradiated on a sample placed in a vacuum chamber to eject atoms or atomic clusters from the surface of the sample (hereinafter, referred to as sputtering). A secondary ion thus generated is measured and the concentration of the impurity in the sample is then calculated.

Next, a raster variation method will be described. The raster variation method is a technique frequently employed in the process to carry out a SIMS analysis on an atmospheric component element (such as H, C, N, or O). When the SIMS analysis is carried on such an atmospheric component element, a background is generated due to any adsorption component on the surface of the sample or the inner wall of the chamber, residual gas in vacuo, or the like. The background may contribute to the detected signal of the secondary ion of the impurity element which is the target of the measurement, thereby degrading the lower detection limit of the measured concentration of the impurity element, or destabilising the detected signal. The raster variation method carries out the measurement of a secondary ion with respect to each of the primary component substance and the impurity element two times while changing the irradiation density of the primary ion to allow the contribution of the background to be separated. If the background can be calculated as described above, the contribution thereof can be canceled from the detection signal so that the concentration of an impurity that is lower than that of the background can be calculated.

[Non-Patent Document 1] TORAY Research Center, "Microanalysis of Atmospheric Component Element in Semiconductor Material" [online]; [retrieved on Jun. 3, 2004], Internet <URL: http://www.toray-research.co.jp/sims/pdf/taikiseibun.pdf>.

DISCLOSURE OF THE INVENTION

Problem to be Solved

However, in SIMS analysis using the conventional raster variation method, because of the sensitive analysis, it is necessary to wait for the stabilization of the intensity of the secondary ion to a constant value after placing the sample in the chamber. In general, a four-hour or longer waiting time is required. Such a waiting time lowers the throughput of the measurement. Therefore, if the waiting time is shortened, an improvement in the throughput of the measurement can be expected.

Means of Solving the Problems

For attaining the objects described above, one aspect of the present invention provides a method that allows measurement of the concentration of an impurity, even during the intensity of the secondary ion is attenuating, by approximating the time-lapse variation in the intensity of the secondary ion. More specifically, the following is provided.

(1) In method for calculating the concentration of an impurity element included in a primary component substance by SIMS, comprising the steps of: calculating by a calculation unit a first dependence of the intensities of secondary ions of the primary component substance and the impurity element upon elapsed time, which are sequentially measured by a measuring unit, on the basis of a first measurement condition during a first measurement period, and a second dependence of the intensities of secondary ions of the primary component substance and the impurity element upon elapsed time, which are sequentially measured by a measuring unit, on the basis of a second measurement condition during a second measurement period; and calculating the concentration of the impurity element by the calculation unit, while providing the calculation unit with the first dependence and the second dependence as inputs, wherein the first measurement condition and the second measurement condition contain primary ion irradiation densities which are different from each other, the difference between the first dependence and the second dependence is substantially constant with respect to the elapsed time in any period of the first measurement, period or the second measurement period.

According to this aspect, for example, the concentration of an impurity element can be measured even during a period wherein the secondary ion is being attenuated with elapsed time, for example, even after setting a sample in a chamber or directly initiating a pressure reduction. More specifically, the measurements of the intensities of secondary ions of the primary component substance and the impurity element are sequentially carried out for a predetermined first measurement period at a predetermined irradiation density of the primary ion, while time-lapse variations thereof are recorded. The time-lapse variations are approximated to obtain a time-lapse variation A and a time-lapse variation B. Such a process is performed again on an irradiation density of another primary ion, which is different from the above measurement, during a predetermined second measurement period different from the first one to obtain both time-lapse variation A' and time-lapse variation B'. At this time, when the difference between A and A' and the difference between B and B' are constant over all of the elapsed times included in the first measurement period and the second measurement period, the concentration of the impurity element can be calculated independently from these elapsed times. As a result, the concentration of the impurity element can be calculated even during a period of measurement in which the intensities of the secondary ions undergo time-lapse variations. Consequently, the waiting time for the measurement can be shortened and an improvement of throughput for the measurement can he expected.

Here, each of the above predetermined first measurement period and the predetermined second measurement period may be a continuous period or a discontinuous period (for example, intermittent period). For instance, the first measurement period may be composed of divided periods with a second measurement period therein. In addition, each of a combination of the time-lapse variation A and the time-lapse variation B and a combination of the time-lapse variation A' and the time-lapse variation B' may be approximate functions capable of mutual extrapolation or extrapolation of one into the other. For instance, the time-lapse variation A can be extrapolated with time-lapse variations in intensity of the secondary ion in the second measurement period with respect to the primary component substance.

(2) A method according to (1), wherein the calculation unit calculates an optimization function that represents the first dependence and the second dependence by a least-squares method.

According to this aspect, for example, an optimization function FA(t) representing a primary component substance and an optimization function FB(t) representing an impurity of the first dependence; and an optimization function FA'(t) representing a primary component substance and an optimization function FB'(t) representing an impurity of the second dependence are calculated by a least-squares method to expect the same effects as these of the aspect (1). Here, at first, after obtaining an optimization equation for FA(t) by the first least-squares method, FA'(t) may be obtained by the second least-squares method using only a zero-order factor (i.e., constant term) as a target of optimization, or FA(t) and FA'(t) may be obtained using one least-squares method by acquiring all of factors including a zero-order factor while assuming that high-order factors other than the zero-order factor (i.e., constant term) are equal to each other. Variations in such procedures may be also applied on FB(t) and FB'(t).

(3) A method according to (2), wherein the type of the optimization function is defined by a control unit based on the first dependence and the second dependence.

According to this aspect, the types of optimization functions that represent the first dependence and the second dependence can be defined, respectively. More specifically, during a process in which the intensity of the secondary ion is greatly attenuated depending on the elapsed time, such as after placing a sample in the chamber or immediately after initiating the pressure reduction in the chamber, each of these dependences may be represented by a relatively higher order polynomial function or a non-polynomial function such as an exponential function, while if the attenuation is small, for example, after more times has elapsed, each of these dependences may be represented by a comparatively lower order polynomial function.

(4) A program for carrying out a method according to any of (1) to (3).

According to this aspect, the same effects as those of (1) to (3) can be expected.

(5) A device for carrying out a method described in any of the above (1) to (3), comprising: the measuring unit, the calculation unit, and a control unit for controlling the measuring unit and the calculation unit.

The use of a device according to this aspect can calculate the concentration of the impurity element by a method described in any of the above (1) to (3).

(6) A device for carrying out a method according to any of (1) to (3), comprising: a SIMS device having the measuring unit, the calculation unit, and a control unit for controlling the SIMS device and the calculation unit.

The use of a device according to this aspect can calculate the concentration of the impurity element by a method described in any of the above (1) to (3).

BRIEF DESCRIPTION OF THE DRAWINGS

FIG. 5 is a view showing the calculation results of the concentration of C at the A region of FIG. 3A.

FIG. 7 is a view showing the calculation results of the concentration of C in the B region of FIG. 3A.

FIG. 10 is a view illustrating the procedures for measuring the concentration of an impurity.

FIG. 12 is a view showing the accuracy results of the measurement concentration of the impurity element in bulk Si.

EXPLANATION OF REFERENCE NUMERALS IN DRAWINGS

Figure 1:
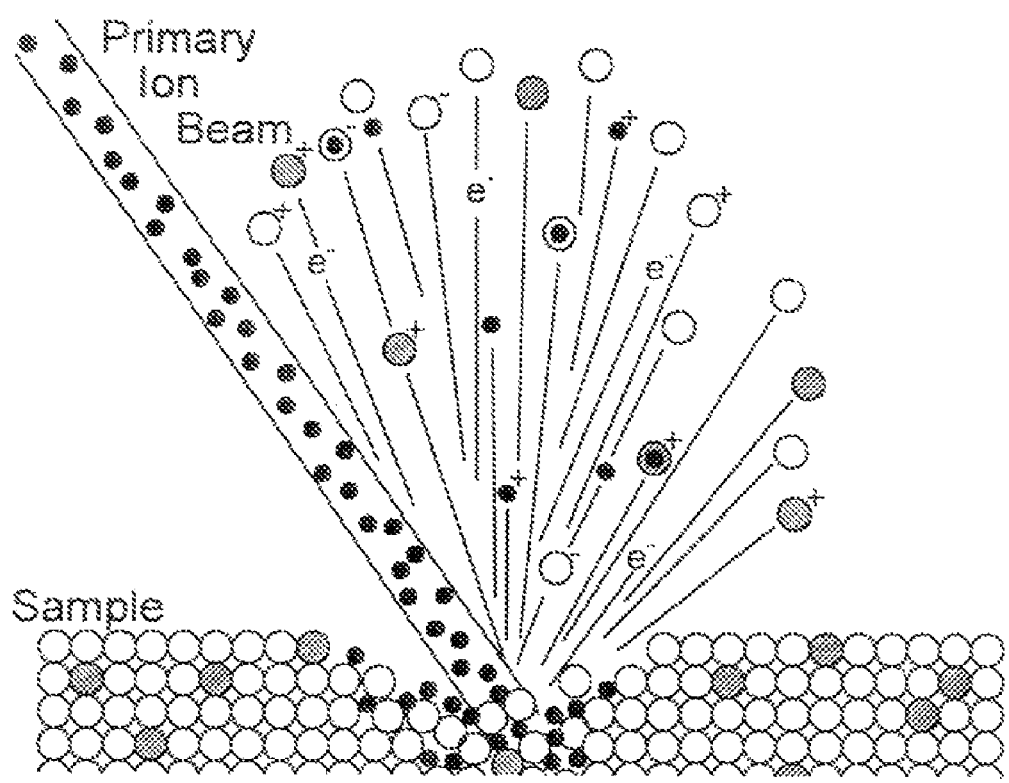
FIG. 1 is a view illustrating the principle of SIMS.

1 SIMS device
2 Calculation unit
3 Control unit
4 Input unit
5 Display unit
6 Memory
7 Storage unit
11 Cesium ion source
12 Duo-plasmatron ion source
13 Primary ion mass filter
14 Primary ion column
15 Air lock system
16 Sample chamber
17 Transfer lens 18 Static analyser
19 Laminate magnet
20 Secondary electron amplifying tube and Faraday cup
21 Ionic image detector
22 CCD camera

PREFERRED MODE FOR CARRYING OUT THE INVENTION

As one example of the present invention, the application thereof to the evaluation of an impurity element C in bulk Si, in which the primary component substance is silicon, will be described. Here, the present invention is not limited to C but applicable to the evaluation of the concentration of any of various impurity elements. Thus, the technical scope of the present invention is not limited by the present embodiments.

Figure 2A:
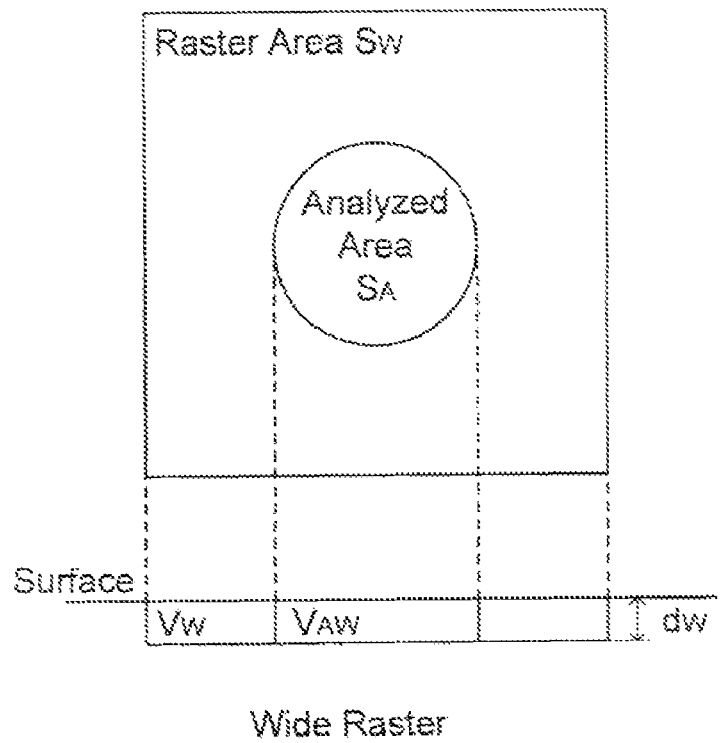
FIG. 2A is a view schematically illustrating the state of a Wide Raster for explaining the principle of a raster variation method.
Figure 2B:
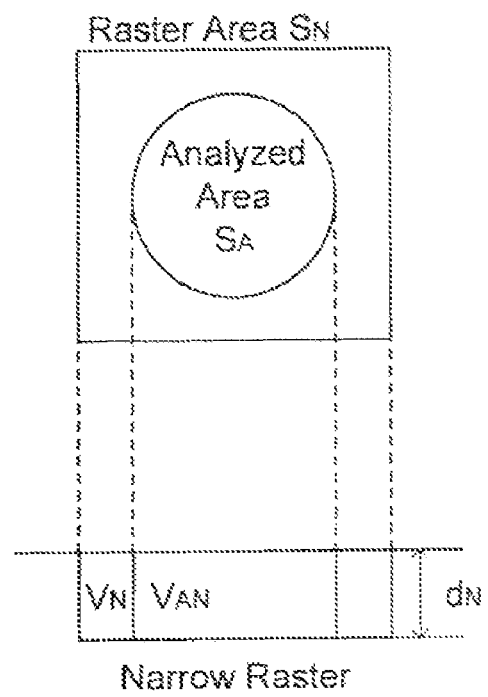
FIG. 2B is a view schematically illustrating the state of the Narrow Raster for explaining the principle of a raster variation method.
Figure 2C:
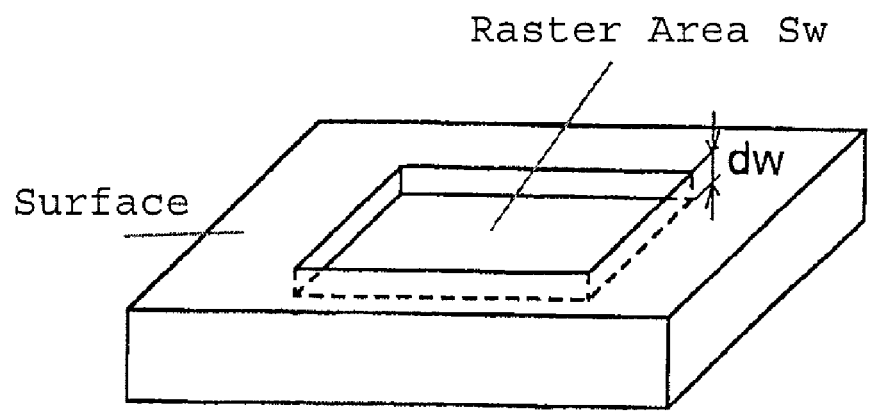
FIG. 2C is a view schematically illustrating the depth when the Wide Raster is used for explaining the principle of a raster variation method.
Figure 2D:
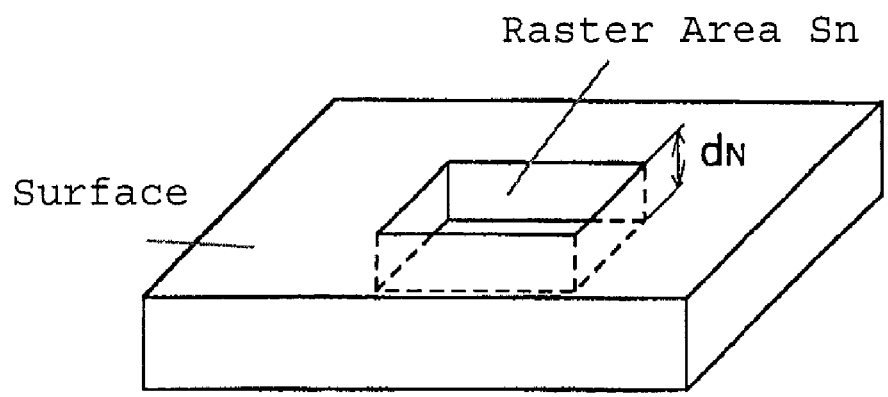
FIG. 2D is a view schematically illustrating the depth when the Narrow Raster is used for explaining the principle of a raster variation method.

FIGS. 2A to 2D show an example of a scanning method for a primary ion beam by a raster variation method applied in the present invention. FIG. 2A represents a raster scanning with a Wide Raster having a relatively lower irradiation density. FIG. 2B represents a raster scanning with a Narrow Raster having a relatively high irradiation density. The total amounts of current of the irradiated primary ions are constant in FIG. 2A and FIG. 2B, but different in the areas subjected to raster scanning. Therefore, the volumes sputtered in FIGS. 2A and 2B are substantially the same, so that the depths of sputter $d_W$, $d_N$ are different (i.e., $d_N$ is deeper than $d_W$). During such a raster variation, the background intensity is considered to be constant, thus, using the raster variation method, the concentration of an element of interest and the backgrounds intensity thereof can be estimated.

The concentration [C] of an impurity (in this case, C) and the concentration [$C_{BG}$] of a background element of interest in the raster variation method are determined as follows;

$$[C] = RSF \times (I_n - I_N)/(I_m - I_M) \quad (1)$$

$$[C_{BG}] = RSF \times I_n/I_m - [C] \quad (2)$$

Here, the term RSF (Relative Sensitivity Factor) is a specific factor defined by the combination of an. impurity element and a primary component substance in the SIMS measurement method, and is widely known. The signal intensity directly measured is $I_n$ (Narrow Raster) and $I_N$ (Wide Raster) for C and $I_m$ (Narrow Raster) and $I_M$ (Wide Raster) for Si. In this way, using the raster variation method, the background can be calculated (Equation 2) and the contribution thereof can be then canceled to allow the concentration of an element of interest to be calculated (Equation 1).

Figure 3A:
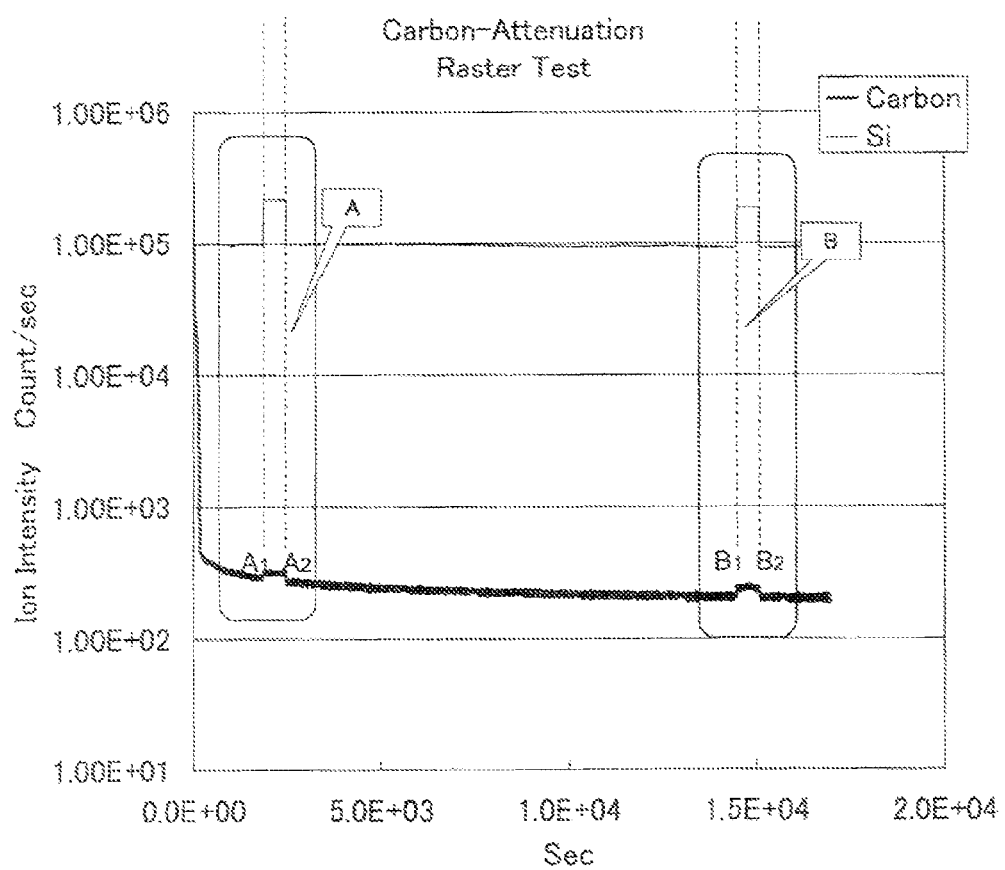
FIG. 3A is a view of an example showing the time-lapse variation of the counted intensity of the SIMS measurement.
Figure 3B:
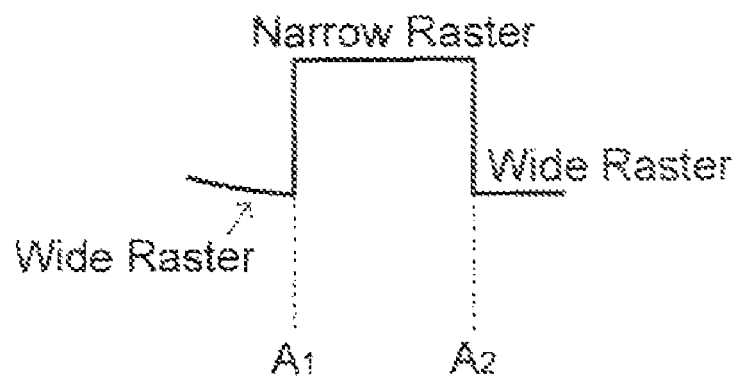
FIG. 3B is a view schematically illustrating the time-lapse variation of the counted intensity of an A region of FIG. 3A.
Figure 3C:
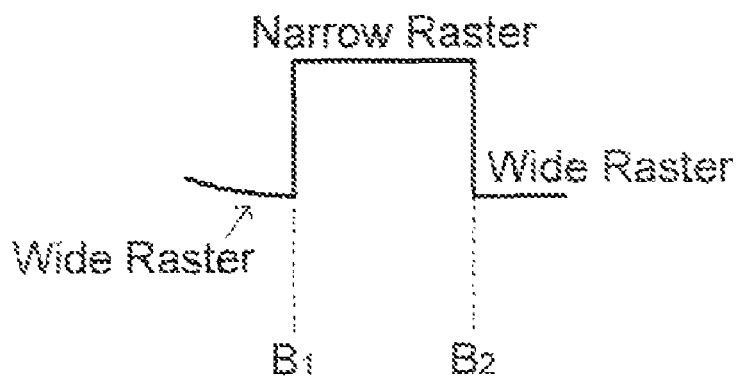
FIG. 3C is a view schematically illustrating the time-lapse variation of the counted intensity of a B region of FIG. 3A.

FIGS. 3A to 3C show an example of the result of measuring a secondary ion of each of a primary component substance Si and an impurity element C. The elapsed time is plotted as the abscissa and the intensity of the secondary ions [counts/sec] of each of the primary component Si and the impurity element C are plotted as ordinates. As is read cut from FIGS. 3A to 3C, in the A region, the intensity of the secondary ion of each of Si and C are attenuated as times advances. In the B region, furthermore, sufficient time has elapsed from the initiation of the reduction of the pressure in the chamber, the intensity of the secondary ions of each of Si and C are almost constant without depending on the elapsed time. For both the A and B regions, there are two steps (the Left Step ($A_1$, $B_1$) and the Right Step ($A_2$, $B_2$)) found in the respective graphs of the measurement results (see, FIGS. 3B and 3C, respectively). However, the irradiation density of the primary ion is changed in each of the steps. More specifically, in the Left Step, the Wide Raster is replaced with the Narrow Raster, and in the Right Step, the Narrow Raster is replaced with the Wide Raster.

Figure 4A:
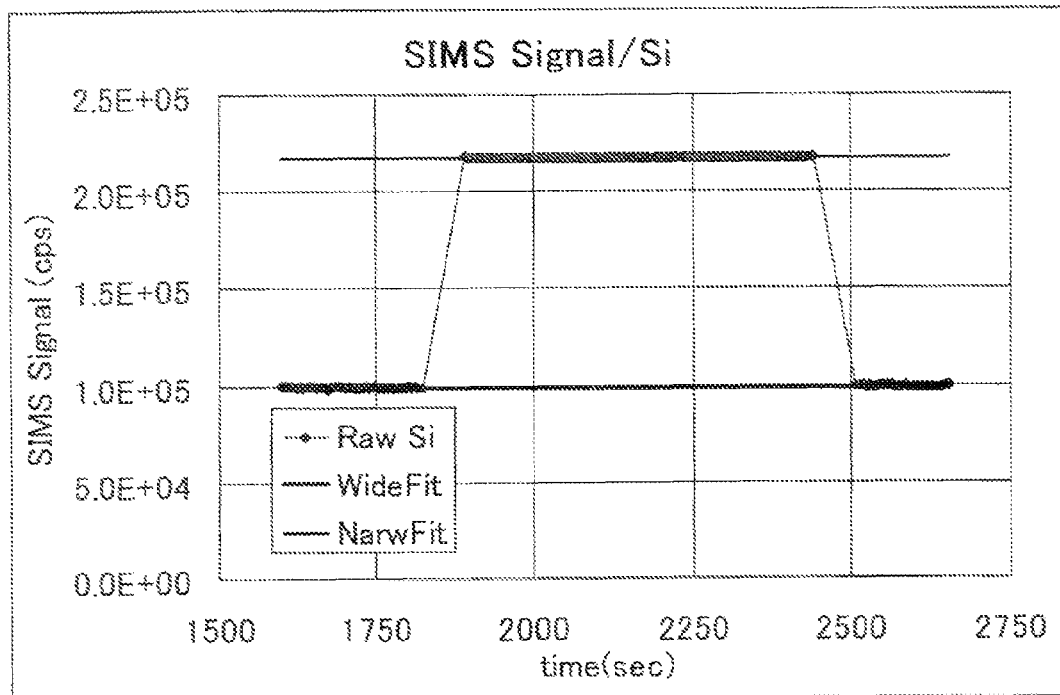
FIG. 4A is an enlarged view showing the time-lapse variation of the Si-counted intensity of the A region of FIG. 3A.
Figure 4B:
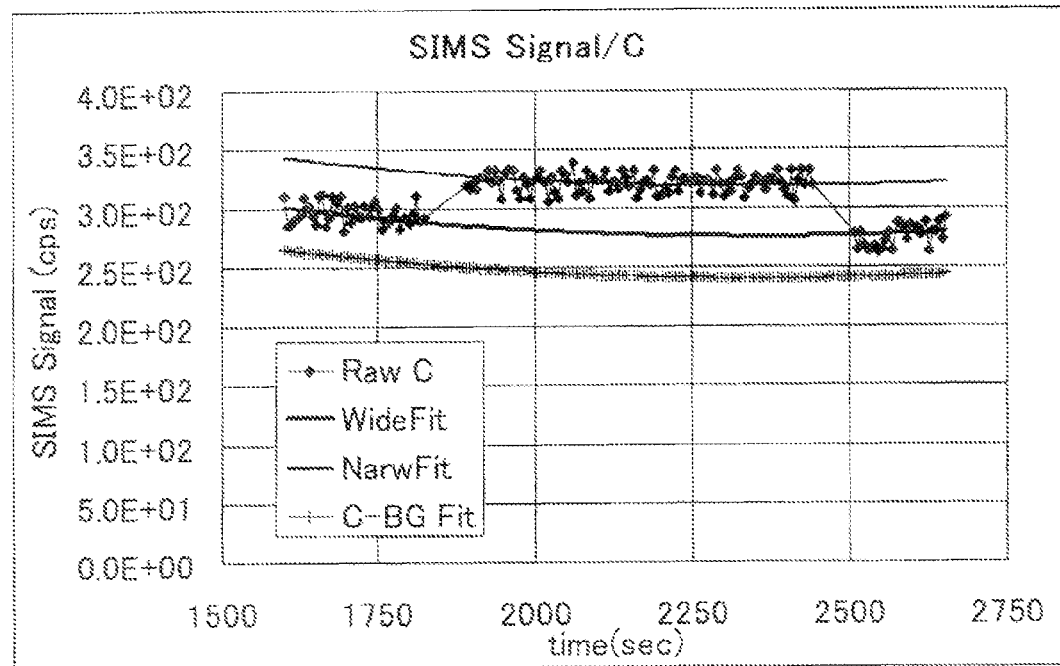
FIG. 4B is an enlarged view showing the time-lapse variation of the C-counted intensity of the A region of FIG. 3A.

FIGS. 4A and 4B are enlarged views of the measurement results in the A region of FIG. 3A. A least-squares method is employed to calculate the Narrow Fit (first dependence, Equation 3) and the Wide Fit (second dependence, Equation 4) for the intensity of Si (counts) and the Narrow Fit (first dependence, Equation 5) and the Wide Fit (second dependence, Equation 6) for the intensity of C as quadratic functions of time (X), respectively. Here, each of the measurement times for the Narrow Fit and the Wide Fit was about 600 seconds. However, it is preferable that a transition time required for transiting from the Narrow Fit to the Wide Fit or from the Wide Fit to the Narrow Fit is not incorporated into the measurement time for obtaining each of the first and the second dependences using approximation because the constant irradiation conditions are hardly obtained and the measured value may not be necessarily stable (the same as below). The least-squares method used herein is a method for obtaining all of the factors including a zero-order factor (i.e., constant term) by performing a least squares fit once while assuming that, the higher order factors other than zero-order are equal to each other. Therefore, the difference between the functions is constant with respect to the elapsed time (or the difference is provided as a constant term).

$$Y = 0.0017X^2 - 7.3189X + 225143 \quad (3)$$

$$Y = 0.0017X^2 - 7.3189X + 106704 \quad (4)$$

$$Y = 4E-05X^2 - 0.2025X + 515.78 \quad (5)$$

$$Y = 4E-05X^2 - 0.2025X + 558.53 \quad (6)$$

FIG. 5 shows the calculation results of the concentration of C at the A region of the present example. Here, in the present example, the background of C and the concentration of C are numerically represented at two clock times among those obtained by carrying out the least squares approximation on the entire interval thereof, a time corresponding to the Left Step and a time corresponding to the Right Step. In this example, the concentration of C shows a constant value over the entire interval.

As a result of applying the raster method on the concentration of C at the A region, [C]=9.38E14 [atoms/cm$^3$] can be calculated at the clock time corresponding to the Left Step ($A_1$) and also at a clock time corresponding to the Right Step ($A_2$). Therefore, it is found that the calculating result of [C]=9.86E14 [atoms/cm$^3$] at the B region (both a clock time corresponding to the Left Step ($B_1$) and a clock time corresponding to the Right Step ($B_2$) of the concentration of C) also correspond well. Here, it is noted that the use of the conventional raster variation method allows the calculation of the concentration of C at the B region, but same calculation cannot be carried on the A region. In this example, the waiting time for the measurement of the intensity of the secondary ion at the A region is 2,000 seconds, while the waiting time for the measurement of the intensity of the secondary ion at the B region is 14,500 seconds. Comparing both waiting times, the waiting time for the same measurement can be reduced by about 3 hours and 28 minutes (86.2%).

Figure 6A:
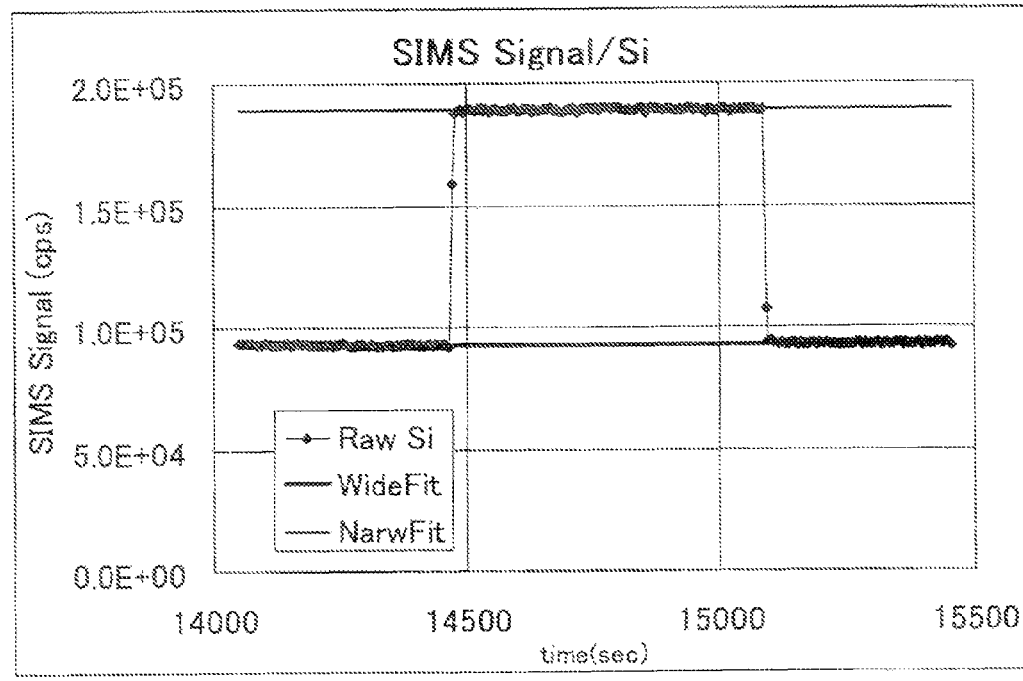
FIG. 6A is an enlarged view showing the time-lapse variation of the Si-counted intensity of the B region of FIG. 3A.
Figure 6B:
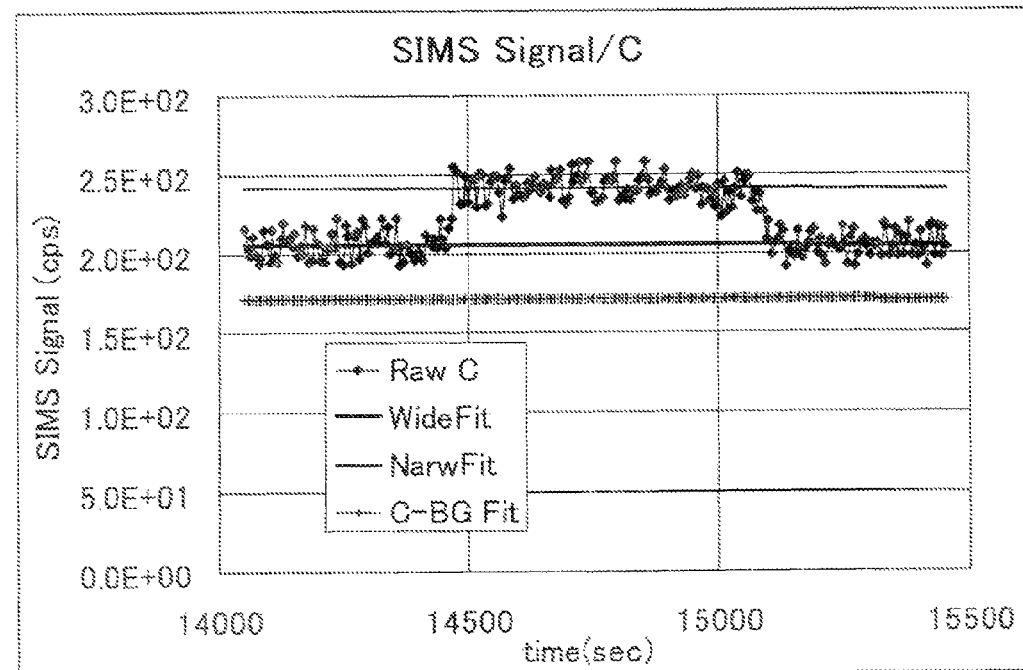
FIG. 6B is an enlarged view showing the time-lapse variation of the C-counted intensity of the B region of FIG. 3A.
Figure 8:
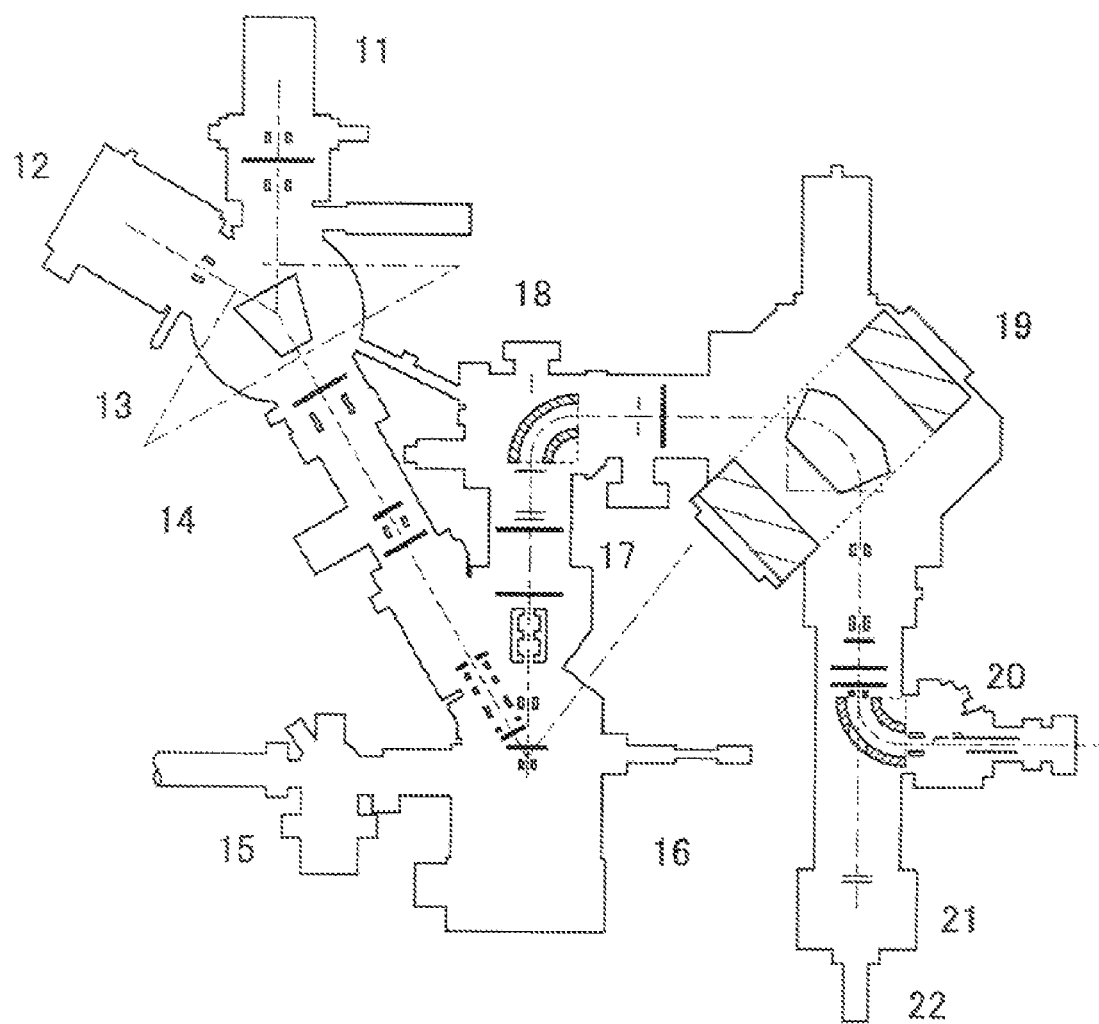
FIG. 8 is a view illustrating an example of a SIMS device that measures the concentration of an impurity.

Enlarged views of the measurement results at the B region in FIG. 3A are shown in FIGS. 6A and 6B, respectively. A least-squares method is employed to calculate the Narrow Fit (first dependence, Equation 7) and the Wide Fit (second dependence, Equation 8) for the intensity of Si (counts) and the Narrow Fit (first dependence. Equation 9) and the Wide Fit (second dependence, Equation 10) for the intensity of C as quadratic functions of time (X), respectively. Here, each of the measurement times for the Narrow Fit and the Wide Fit was about 600 seconds each. The least-squares method used herein is a method for obtaining all of the factors including a zero-order by performing a least squares calculation once while assuming that higher-order factors other than zero-order are equal to each other. Therefore, the difference between the functions is constant with respect to the elapsed time.

$$Y=0.0009X^2-25.376X+375867 \quad (7)$$

$$Y=0.0009X^2-25.376X+279254 \quad (8)$$

$$Y=-1E-06X^2-0.0352X+48.64 \quad (9)$$

$$Y=-1E-06X^2-0.0352X-12.875 \quad (10)$$

FIG. 7 shows the calculation results of the concentration of C at the a region. Here, in the present example, the background of C and the concentration of C are numerically represented at two clock times, a time corresponding to the Left Step and a time corresponding to the Right Step. In this example, the concentration of C shows a constant value over the entire interval.

Here, it is found that the concentration of an impurity as described above can be calculated if the intensities of the secondary ions with respect to the two or more irradiation densities are measured. In other words, in the case of not representing by a zero-order function but representing by a higher-order polynomial function or a nonpolynominal function such as an exponential function, as described above, a measurement may be carried exit only one time for each of the Narrow Raster and the Wide Raster (i.e., switched once) instead of a method that switches two times between the irradiation densities of two different primary ions, for example switching from the Wide Raster to the Narrow Raster and then switching back from the Narrow Raster to the Wide Raster. Furthermore, any method that switches modulation wave forms, including sine waves and rectangular waves for the irradiation density of the primary ion may be used.

In addition, for example, the measurement of the secondary ion intensities of silicon and nitrogen are conducted during a predetermined time with a predetermined irradiation density of the primary ion, and a time-lapse variation is approximated using appropriate functions (such as functions of first, second, and multiple orders, and an exponential function). Then, a time-lapse variation A and a time-lapse variation B are obtained, respectively. Furthermore, a different predetermined period, and a different primary ion irradiation density from the prior procedures are employed, and then a time-lapse variation A' and a time-lapse variation B' are obtained using the respective approximation formulae in a similar manner. At this time, if the difference between A and A' and the difference between B and B' are constant, the concentration of nitrogen independent of an elapsed time can be calculated. Therefore, even in the measurement time period where the secondary ion intensity varies as time-lapsed, the concentration of the impurities can be calculated, so that the waiting time for the measurement can be shortened and an improvement in the throughput of the measurement can be obtained.

FIG. 3 shows an example of a SIMS device for carrying out the present invention. A primary ion composed of cesium, ions generated from a cesium ion source 11 or oxygen ions generated from a duo-plasmatron ion source 12 is irradiated on a sample placed in a sample chamber 16 being kept at ultra-high-vacuum to allow the primary ion to collide against the surface of the sample. The collision separates and ejects atoms or atomic clusters from the sample (sputtering). Most of such atoms and atomic clusters are neutral, but some of them may be charged positively or negatively. These secondary ions may be released from about 1 nm in depth from the surface of the sample. Then, secondary ions positively or negatively charged is accelerated and transferred to a mass spectrography through a transfer lens 17, whereby they are separated based on a ratio of mass and charge. Subsequently, only secondary ions having a specific ratio of mass/charge will be detected by the secondary electron amplifying tube and Faraday cup 20. Data of the detection results is transferred to a general-purpose computer and then the data thus collected is expressed as an element map on the surface of the sample or a profile for the depth direction of the composition of the sample.

Here, the intensity of the ion beam current and the beam diameter of primary ion generated from an ion source can be controlled by an electrostatic lens, and the current density of the beam can be thus controlled. In addition, a deflector performs the centering of the ion beam and raster-scanning.

Figure 9:
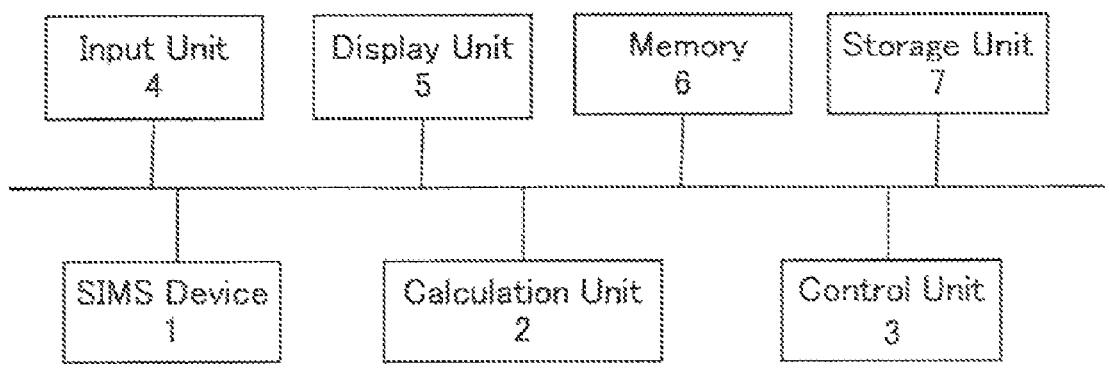
FIG. 9 is a view illustrating an example of the general configuration of a device that measures the concentration of an impurity.

FIG. 9 shows an example of the general configuration of the apparatus for carrying out the present invention. The general configuration of the apparatus comprises a SIMS device 1, a calculation unit 2, an input unit 4, a display unit 5, a memory 6, a storage unit 7, and a control unit 3 for controlling these units. The control unit 3 controls the series of procedures described in FIG. 10.

FIG. 10 shows the procedures for determining the concentration of an impurity in accordance with the present invention. First, an irradiation unit irradiates primary ion having a predetermined first irradiation density onto the surface of a primary component substance based on the control of the control unit (Step S1). Then, a measuring unit sequentially performs the measurements of the intensities of secondary ions of the primary component substance and the impurity element during the first predetermined measurement period based on the control of the control unit (Step S2). The irradiation unit irradiates primary ions having a second irradiation density, which is different from the first irradiation density, onto the surface of the primary component substance based on control by the control unit (Step S3). The measuring unit sequentially carries out the measurement of the intensity of a secondary ion for each of the primary component substance and the impurity element during the second measurement period based on the control unit (Step S4). The calculation unit calculates a first dependence on the elapsed time of the intensity of a secondary ion of each of the primary component substance and the impurity element during the first measurement period (Step S5). Based on the control of the control unit, the calculation unit calculates a second dependence on the elapsed time of the intensity of a secondary ion of each of the primary component substance and the impurity element during the second measurement period (Step S5). The calculation unit calculates the concentration of the impurity element based on control of the control unit using the first dependence and the second dependence as inputs (Step S7).

The applicable scope of the present invention is not limited to the examples described above. The present invention can be applied to all elements that can be detected by SIMS, for example, the primary component substances include Ge, GaAs, and SiGe; impurity substances include atmospheric elements N, O, H, C, and He; those used as dopants of Si include Boron, P, As, and Sb; metals include Al, Ni, Fe, Cu, and Cr; and substances having high dispersion rates in Si include Li, Na, X, Au, Co, Zn, Ag, Ir, Pt, S, Se, and Ti. In addition, in the above example, the irradiation density of a primary ion can be changed by changing the raster-scanning area. Alternatively, the raster-scanning area may be kept constant, while the amount of the primary ion generated per unit of time may be changed to realise the present invention. In addition, without depending on the raster scanning, the present invention may be carried out by changing the beam diameter of the primary ion. Furthermore, in the above example, the first dependence and the second dependence are represented by an X-order polynomial expression, but in the present invention, any function, such as an exponential function, may be used.

EXAMPLE 1

Figure 11A:
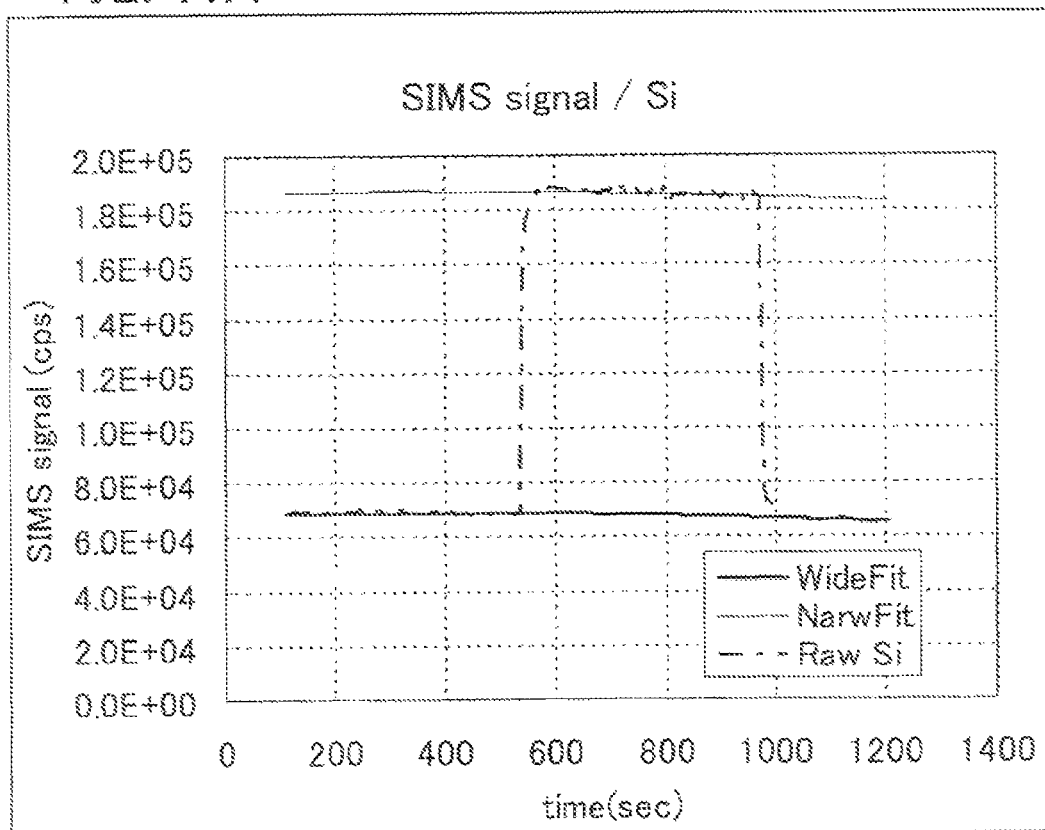
FIG. 11A is a view illustrating an experimental example (Si) in which a raster variation method is applied in a SIMS measurement.
Figure 11B:
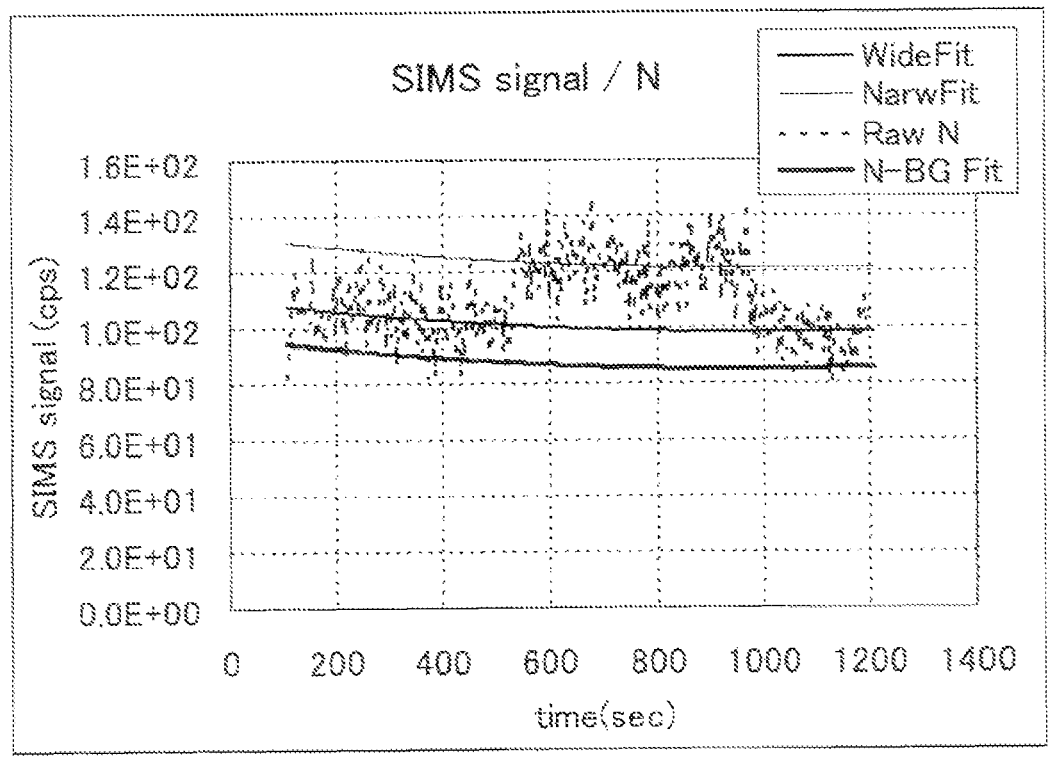
FIG. 11B is a view illustrating an experimental example (N) in which a raster variation method is applied in a SIMS measurement.

FIGS. 11A and 11B show an example in which a first dependence and a second dependence are calculated as a quadratic function by a least-squares method in the evaluation of the concentration of an impurity element n in bulk Si, where the primary component substance is silicon. A least-squares method is employed to calculate a Narrow Fit (first dependence. Equation 11) and a Wide Fit (second dependence, Equation 12) for the intensity of Si (counts) and a Narrow Fit (first dependence, Equation 13) and a Wide Fit (second dependence, Equation 14) for the intensity of N as quadratic functions of time (X). Here, the least-squares method used herein is a method for obtaining all the factors including a zero-order factor by performing a least squares calculation once. Therefore, the difference between the functions is constant with respect to the elapsed time.

$$Y = -0.0046X^2 + 2.9082X + 186410 \quad (11)$$

$$Y = -0.0046X^2 + 2.9082X + 68364 \quad (12)$$

$$Y = 1E-05X^2 - 0.0236X + 132.96 \quad (13)$$

$$Y = 1E-05X^2 - 0.0236X + 110 \quad (14)$$

The concentration of N calculated in this example is $[N] = 3.82E+14$ [atoms/cm$^3$].

In this example, the following device was used;
SIMS measuring device; IMS-6F (CAMECA)
In addition, the measuring conditions used were as follows:
Types of primary ions: Cs, O (changed depending on the measurement target).
Acceleration voltage for the primary ion: 10 to 15 kV.
Primary ion current: ~100 nA.
Detected secondary ion: atmospheric elements, such as C, Si, N, and Cu.
Raster areas: small=about 100 μm$^2$, large=about 180 μm$^2$.
Areas of analysis: ~30 μmΦ.

EXAMPLE 2

The measurements of carbon (C), copper (Cu), and nitrogen (N) were carried out under the same conditions as those of Example 1. Consequently, the results shown in FIG. 12 were obtained. In the right columns, 99% confidence limit values, which were obtained when the results of the above measurements were used for the treatments on narrow and wide areas, were listed. The results obtained from the differences between the cases of only treating the narrow areas and the values of the present invention are listed in the left columns.

$$[C] = RSF \times (I_n - I_N)/(I_m - I_M) \quad (1)$$

$$[C_{BG}] = RSF \times I_n/I_m - [C] \quad (2)$$

These values are average values. Therefore, the application of the present invention further lowers the lower limits of quantitative estimation of the concentration of the impurity of interest, so that the measurement can be performed on a smaller concentration, compared with the conventional measurements. In particular, it is proved that the 99% confidence limit values become better than the error only treating the narrow region by half digit to two digits. The accuracy can be enhanced compared with quantitative analysis using one of the narrow and wide areas.

Here, both the first measurement period and the second measurement period will be briefly described. These settings are defined in consideration of desired accuracy and throughput (performance). In addition, it may vary depending on the substance of interest. In the above examples (Examples 1 and 25, the measurements are carried out with the narrow and the wide area for 5 minutes, respectively. The amount of the data detected in the meantime is in proportion to the time period of the measurement. For example, when less accuracy is desired, the measurement may be completed over a shorter time period.

According to the present invention, even in a period wherein the secondary ion is attenuated over time in the step of vacuum waiting, for example, just after setting a sample on a SIMS measuring device, the concentration of an impurity element can be measured. As a result, the waiting time for the measurement can be shortened and the throughput of the measurement can be increased.

The invention claimed is:

1. A method for calculating the concentration of an impurity element included in a primary component substance by Secondary Ion Mass Spectroscopy (SIMS), the method comprising:
    performing a measurement, including:
        performing a first measurement (S1, S2) that sequentially measures intensities of secondary ions of the primary component substance and the impurity element on the basis of a first measurement condition in which primary ions are irradiated at a first irradiation density during a first measurement period, and
        performing a second measurement (S3, S4) that sequentially measures intensities of secondary ions of the primary component substance and the impurity element on the basis of a second measurement condition in which primary ions are irradiated at a second irradiation density during a second measurement period, such that a total amount of current is identical to that in the first measurement condition; and
    performing a calculation using a calculation module of a computer, including:
        performing, using the calculation module, a first calculation (S5, S6) that calculates a first dependence that approximates time-lapse variation of the intensities, obtained by the first measurement (S1, S2), of the secondary ions of the primary component substance and the impurity element, and a second dependence that approximates time-lapse variation of the intensities, obtained by the second measurement (S3, S4), of the secondary ions of the primary component substance and the impurity element, and
        performing, using the calculation module, a second calculation (S7) that calculates the concentration of the impurity element being independent of elapsed time by using the first dependence and the second dependence.

2. A method according to claim 1, wherein
    the first calculation (S5, S6) is performed such that difference of the primary component substance between the first dependence and the second dependence and difference of the impurity element between the first dependence and the second dependence are constant relative to the elapsed time for each measurement by the first measurement (S1, S2) and the second measurement (S3, S4).

3. A method according to claim 2, wherein
the first calculation (S5, S6) obtains an optimization function that represents the first dependence and the second dependence by a least-squares method.

4. A method according to claim 1, wherein
the first dependence includes a relatively low primary ion irradiation density condition, and the second dependence includes a relatively high primary ion irradiation density condition; and
the measurement steps (S1 to S4) include measurement of intensities of secondary ions, involving switching ion irradiation densities from a first step of irradiating primary ions having relatively low irradiation density, to a second step of irradiating primary ions having relatively high irradiation density, and further switching from the second step to the first step.

5. A non-transitory computer readable recording medium encoded with a program for calculating the concentration of an impurity element included in a primary component substance by SIMS, the recording medium comprising instructions for causing a data processor to:
perform measurement processes including:
a first measurement that sequentially measures intensities of secondary ions of the primary component substance and the impurity element on the basis of a first measurement condition in which primary ions are irradiated at first irradiation density during a first measurement period, and
a second measurement that sequentially measures intensities of secondary ions of the primary component substance and the impurity element on the basis of a second measurement condition in which primary ions are irradiated at second irradiation density during a second measurement period, such that a total amount of current is identical to that in the first measurement condition; and
perform calculation processes including:
a first calculation that calculates a first dependence that approximates time-lapse variation of the intensities, obtained by the first measurement, of the secondary ions of the primary component substance and the impurity element, and a second dependence that approximates time-lapse variation of the intensities, obtained by the second measurement, of the secondary ions of the primary component substance and the impurity element, and
a second calculation that calculates the concentration of the impurity element being independent of elapsed time in the first dependence and the second dependence.

6. A non-transitory computer-readable recording medium according to claim 5, wherein
the first calculation is performed such that difference of the primary component substance between the first dependence and the second dependence and difference of the impurity element between the first dependence and the second dependence are constant relative to the elapsed time for each measurement by the first measurement and the second measurement.

7. A non-transitory computer-readable recording medium according to claim 6, wherein
the first calculation obtains an optimization function that represents the first dependence and the second dependence by a least-squares method.

8. A non-transitory computer-readable recording medium according to claim 5, wherein
the first dependence includes a relatively low primary ion irradiation density condition, and the second dependence includes a relatively high primary ion irradiation density condition; and
the measurement processes include measurement of intensities of secondary ions, involving switching ion irradiation densities from a first process of irradiating primary ions having relatively low irradiation density, to a second process of irradiating primary ions having relatively high irradiation density, and further switching from the second process to the first process.

9. A device for calculating the concentration of an impurity element included in a primary component substance by SIMS, the device comprising:
a measurement unit configured to perform:
a first measurement that sequentially measures intensities of secondary ions of the primary component substance and the impurity element on the basis of a first measurement condition in which an irradiation unit irradiates primary ions at first irradiation density during a first measurement period, and
a second measurement that sequentially measures intensities of secondary ions of the primary component substance and the impurity element on the basis of a second measurement condition in which the irradiation unit irradiates primary ions at second irradiation density during a second measurement period, such that a total amount of current is identical to that in the first measurement condition;
a calculation unit configured to perform:
a first calculation that calculates a first dependence that approximates time-lapse variation of the intensities, obtained by the first measurement, of the secondary ions of the primary component substance and the impurity element, and a second dependence that approximates time-lapse variation of the intensities, obtained by the second measurement, of the secondary ions of the primary component substance and the impurity element, and
a second calculation that calculates the concentration of the impurity element being independent of elapsed time by using the first dependence and the second dependence; and
a control unit configured to control the first and second irradiation densities by the irradiation unit, the first and second measurement by the measurement unit, and the first and second calculation by the calculation unit.

10. A device according to claim 9, wherein
the calculation unit performs the first calculation such that difference of the primary component substance between the first dependence and the second dependence and difference of the impurity element between the first dependence and the second dependence are constant relative to the elapsed time for each measurement by the first measurement and the second measurement.

11. A device according to claim 10, wherein
the calculation unit obtains, in the first calculation, an optimization function that represents the first dependence and the second dependence by a least-squares method.

12. A device according to claim 9, wherein
the first dependence includes a relatively low primary ion irradiation density condition, and the second dependence includes a relatively high primary ion irradiation density condition; and
the measurement unit can perform measurement of intensities of secondary ions, involving switching ion irradiation densities from a first step of irradiating primary ions having relatively low irradiation density, to a second step of irradiating primary ions having relatively high irradiation density, and further switching from the second step to the first step.

* * * * *